(12) United States Patent
Boer De et al.

(10) Patent No.: US 6,645,494 B1
(45) Date of Patent: Nov. 11, 2003

(54) ANTI-CD40L IMMUNOTOXINS FOR THE TREATMENT OF DISEASES

(75) Inventors: Mark Boer De, Blaricum (NL); Marcel Theodorus Hartog Den, Monnickendam (NL)

(73) Assignee: Tanox Pharma B.V., Amsterdam (NL)

( * ) Notice: Subject to any disclaimer, the term of this patent is extended or adjusted under 35 U.S.C. 154(b) by 0 days.

(21) Appl. No.: 09/446,351

(22) PCT Filed: Jun. 22, 1998

(86) PCT No.: PCT/NL98/00357

§ 371 (c)(1),
(2), (4) Date: Feb. 7, 2000

(87) PCT Pub. No.: WO98/58678

PCT Pub. Date: Dec. 30, 1998

(30) Foreign Application Priority Data

Jun. 20, 1997 (EP) ............................................. 97201895

(51) Int. Cl.[7] ........................ A61K 39/395; C07K 16/28
(52) U.S. Cl. ................. 424/183.1; 424/130; 424/133.1; 424/135.1; 424/141.1; 424/143.1; 424/144.1; 424/153.1; 424/154.1; 424/173.1; 424/178.1; 424/179.1; 530/387.1; 530/387.3; 530/388.1; 530/388.2; 530/388.22; 530/388.7; 530/388.73; 530/388.75; 530/391.1; 530/391.7
(58) Field of Search .......................... 424/141.1, 143.1, 424/130.1, 153.1, 178.1; 530/387.1, 388.2, 388.73, 391.1

(56) References Cited

U.S. PATENT DOCUMENTS 5,474,771 A     12/1995   Lederman et al.

FOREIGN PATENT DOCUMENTS

| EP | 0555880 | | 8/1993 |
|---|---|---|---|
| WO | 9426910 | * | 11/1994 |
| WO | 9623071 | * | 8/1996 |
| WO | WO 9717446 | | 5/1997 |

OTHER PUBLICATIONS

Skolnick et al. Trends in Biotechnology 18:34–39 (2000).*
Ngo et al. in the Protein Folding Problem and Tertiary Structure Prediction 1994 Merz et al. (Ed) Birkhauser, Boston, MA pp. 433, 492–495.*
Bolognesi et al. Planta 203: 422–429 (1997).*
Francisco, J. A. et. al.: "Construction, expression . . . etc." *The Journal of Biological Chemistry*, vol. 272, No. 39, Sep. 1997, pp. 24165–24169.
Francisco, J. A. et. al.: "In vivo efficacy . . . etc." *Blood*, Jun. 15, 1997, pp. 4493–4500.
Preijers, F. W.: "Rationale for the clinical . . . etc." *Leukemia and Lymphoma*, (Mar. 1993) 9 (4–5) 293–304. Ref.: 101 Journal Code: BNQ. ISSN: 1042–8194.
Gerritse, K. et. al.: "CD40–CD40 ligand interactions . . . etc." *Proceedings of the National Academy of Sciences of the United States of America*, (Mar. 19, 1996) 93 (6) 2499–504. Journal Code: PV3. ISSN: 0027–8424.

* cited by examiner

*Primary Examiner*—Phillip Gambel
(74) *Attorney, Agent, or Firm*—Handal & Morofsky (57) ABSTRACT

An immunotoxin molecule is described which comprises an antibody specific for human CD40L antigen located on the surface of a human cell, coupled to a toxin molecule or active fragment thereof, wherein the binding of the immunotoxin to the CD40L molecule results in the killing of the CD40L expressing cell. The toxin molecule is especially a type-1 ribosome inactivating protein, or an active fragment thereof. The immunotoxin can be used for the treatment of autoimmune diseases such as multiple sclerosis, rheumatoid arthritis and systemic lupus erythematosus, or T-cell malignancies.

11 Claims, 3 Drawing Sheets

SEQUENCE LISTING

<160> NUMBER OF SEQ ID NOS: 2

<210> SEQ ID NO 1
<211> LENGTH: 149
<212> TYPE: PRT
<213> ORGANISM: Bougainvillea spectabilis

<400> SEQUENCE: 1

-continued

```
Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
            35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
            85                  90                  95

Lys Leu Phe Pro Gly Val Thr Asn Arg Val Thr Leu Thr Phe Asp Gly
            100                 105                 110

Ser Tyr Gln Lys Leu Val Asn Ala Ala Lys Val Asp Arg Lys Asp Leu
            115                 120                 125

Glu Leu Gly Val Tyr Lys Leu Glu Phe Ser Ile Glu Ala Ile Trp Gly
    130                 135                 140

Lys Thr Gln Asn Gly
145

<210> SEQ ID NO 2
<211> LENGTH: 13
<212> TYPE: PRT
<213> ORGANISM: Homo sapiens

<400> SEQUENCE: 2

His Ser Leu Gly Lys Trp Leu Gly His Pro Asp Lys Phe
1               5                   10
```

ANTI-CD40L IMMUNOTOXINS FOR THE TREATMENT OF DISEASES

This application is a Rule 371 Application of PCT Application No. PCT/NL98/00357 (Publication No. WO 9858678), filed on Jun. 22, 1998 which claims priority to EP 97201895.6, filed on Jun. 20, 1997.

FIELD OF THE INVENTION

This invention relates to methods of treating diseases of in which the immune system is involved. In particular, this invention relates to methods of treating T-cell mediated autoimmune diseases such as multiple sclerosis and various malignancies of lymphoid origin.

BACKGROUND OF THE INVENTION

Immunotoxins:

Immunotoxins are chimeric molecules in which cell-binding ligands are coupled to toxins or their subunits. The ligand portion of the immunotoxin is usually a monoclonal antibody (Mab) that binds to selected target cells. The toxin portion of the immunotoxin can be derived form various sources. Most commonly, toxins are derived from plants or bacteria, but toxins of human origin or synthetic toxins (drugs) have been used as well. Toxins used for immunotoxins derived from plants or bacteria all inhibit protein synthesis of eukaryotic cells. The most widely used plant toxin ricin, consist of two disulfate-linked polypeptides A and B (Olsnes et al., in *Molecular Action of Toxins and Viruses* p51–105 (1982)). The most widely used bacterial toxin is Pseudomonas exotoxin (PE). Pseudomonas exotoxin is produced by the bacterium as a single-chain protein (Allured et al., *Proc. Natl. Acad. Sci. USA* 83:1320 (1986)). Another group of plant-derived toxins used in ITs are single-chain proteins (type I RIP), frequently found in plants and have similar enzymatic properties as the A-chain of ricin (reviewed in Stirpe and Barbieri *FEBS Lett.* 195:1 (1986)), these type I RIP however lack the B-chain. The absence of binding activity and as a consequence the inability of the native toxin to bind to cells significantly decreases the non-specific toxicity and makes these toxins extremely interesting for usage in ITs. To target these toxins to potential harmful cells, they are coupled to a Mab against a specific protein on the surface of these targeted cells. The cross-linker used to join the Mab and the toxin must remain stable extracellular, but after internalization of the conjugate into the cell, be labile intracellular so that the toxin fragment can be released in the cytosol and target to the appropriate intracellular location. A complete Mab consists of two heavy and two light chains and can be chemically coupled to the toxin. Using this chemical coupling usually several toxin molecules are coupled to one Mab molecules, resulting in protein complexes of considerable size. An alternative to complete Mabs, is to use single-chain antibody fragments (scFv), which consist of only the variable part of the heavy chain (VH) and the variable part of the light chain (VL) coupled via a short linker (Pastan et al., *Annu. Rev. Biochem.* 61:331 (1992)). The usage of scFv-ITs has a number of advantages compared to chemically coupled ITs. First, the scFv can be cloned via a short linker to a toxin and can be expressed as fusion-protein in a bacterial expression system. Secondly, tissue penetration is a major obstacle when chemical coupled IT-conjugates were used in various animal models, the scFv format being superior in this respect. The use of a scFv as ligand portion of an immunotoxin reduces the size of ligand portion with a factor 6 as compared to a complete Mab and in these recombinant molecules one toxin molecule is linked to one scFv reducing the size even further. Since a scFv-IT is produced as one molecule unwanted cleavage of the toxin and the ligand in the circulation can not occur. The capability of scFv-ITs to specifically eliminate cells, revealed that intracellular cleavage of the ligand and toxin part, that is necessary when ITs are used, is not necessary for the cytotoxic effect of certain scFv-ITs.

Various types of immunotoxins directed against different cellular targets have been evaluated in vivo, both in animal models and in phase I or II clinical trials. The vast majority of clinical studies with immunotoxins has been performed for anti-tumor therapy using ricin A chain or blocked ricin (Frankel et al., *Leukemia and Lymphoma* 26:28 (1997), Lynch et al., *J. Clin. Onc.* 15:723 (1997)). Reports on the administration of immunotoxins containing type I RIPs are limited. Thusfar only two studies have been published, the first using saporin-S6 coupled to an anti-CD30 Mab (Falini et al., *Lancet* 339:1195 (1992)) and the second using the PAP toxin coupled to an anti-CD19 Mab (Uckun et al., *Blood* 79:3369 (1992)). An increasing number of preclinical studies using immunotoxins containing various different type I RIPs (momordin, gelonin, saporin, bryodin and bouganin) are currently under development.

The CD40L Molecule:

The CD40L molecule belongs to the TNF/CD40L gene family (Armitage et al., *Curr. Opin. Immunol.* 6:407 (1994)). Although TNF is a soluble cytokine, it is initially synthesized as a membrane associated molecule. Most of the members of the of the TNF/CD40L receptor family are type II transmembrane proteins. Initially it was reported that the expression of the CD40L was restricted to activated $CD4^+$ T cells. Now it has also been detected on B cells from autoimmuine patients, on mast cells and on baophils. The cell surface expression of CD40L is tightly regulated, specific signals are needed for its appearance and, once engaged with CD40 the molecule rapidly disappears again.

Autoimmune Diseases:

A normal functioning immune system has self-regulating mechanisms to terminate the immune response when it is no longer needed. When these self-regulatory mechanisms become compromised, a person may develop a so-called autoimmune disease. Examples of autoimmune diseases are rheumatoid arthritis, multiple sclerosis, type I diabetes, lupus, thyroiditis, systemic lupus erythematosus and myasthenia gravis.

Multiple sclerosis (MS) is a severely disabling progressive neurological disease, involving autoimmune attack against myelin in the central nervous system. MS affects 1 in 1000 in the USA and Europe. Due to improved diagnosis that number is currently increasing. Onset of disease is usually around 30 years of age and, on average, patients are in need of treatment for another 28 years. Diagnosis of exacerbations and early identification of onset of exacerbations has improved greatly, allowing design of novel treatment strategies. Recently, the involvement of the CD40L molecule in the pathophysiology of MS has been demonstrated using the experimental allergic encephalomyelitis model in mice (Gerritse et al., *Proc. Natl. Acad. Sci. USA* 93:2499 (1996)). In this model, injection of mice with a blocking monoclonal antibody (Mab) to CD40L at the time of disease induction, completely prevents disease. Furthermore, in situ analysis of CD40L and CD40 in human MS brain has revealed that CD40 expression is abundantly expressed on macrophages in perivascular infiltrates. Frequencies of CD40L positive cells in these infiltrates were modest, but could be found in juxtaposition to CD40 positive cells, indicative of an ongoing cellular interaction.

Systemic lupus erythematosus (SLE) is an other autoimmune disease in which the CD40L molecule has been implicated. SLE, in contrast to most autoimmune diseases, has the potential to involve multiple organs. The clinical manifestations of SLE are extremely variable and diverse. Some patients only have mild involvement of skin and joints, require little medication and show spontaneous remissions. Whereas other patients suffer from severe and progressive glomerulonephritis that in the end does not even respond to high doses steroids and cyclophosphamide. SLE can manifest at nearly any age, but the disease onset is usually between 15 and 50 years. SLE affects about 8 times more females than males. The chance that a caucasian women in her life time develops SLE is about 1 in 700, whereas this incidence can be two to four times higher in hispanics or blacks. The overall prevalence of SLE is in the order 1 in 2000. SLE is characterized by a production of high affinity IgG antibodies to self antigens (autoantibodies). The principal targets of autoantibodies in SLE include certain protein-nucleic acid complexes. The multivalent nature of these complexes and their ability to cross-link B-cell receptors have been proposed as explanations for their strong immunogenicity. However, the mechanism by which these autoantibodies cause disease is still unclear. Autoantibodies to phospholipids are also frequently found and are associated with thrombotic complications. Also autoantibodies to cell surface molecules can be found. These target specificities are easier to understand with respect to the pathology, causing problems such as hermolytic anemia and platelet destruction. In contrast to autoimmune diseases such as RA and MS, T cells do not appear to play a direct role in tissue damage in SLE, although the do play an important role in the production of autoantibodies. The induction of the CD80/86 molecules on autoantigen-specific B cells by autoantigen-specific helper T cells via the CD40L-CD40 interaction represents a critical step in the maturation and subsequent differentiation of autoantigen-specific B cells. Recently it was observed that both T cells and also B cells from active SLE patients show a constitutive expression of CD40L (Desai-Metha et al., *J. Clin. Invest.* 97:2063 (1996)).

SUMMARY OF THE INVENTION

Activated T cells are specifically involved in the pathophysiology of autoimmune diseases such as MS and SLE. The onset of an exacerbation in autoimmune patients is believed to started when autoreactive T cells are activated. This antigen-specific activation results in the express significant amounts of CD40L on the cell surface. This has led several groups to explore the physical blocking of the CD40L-CD40 interaction as a treatment modality for auto immune diseases. However, it may be expected that after withdrawal of the therapeutic molecule that blocks the CD40L-CD40 interaction, the disease can return to the same magnitude or even more severe as before the treatment. As an alternative, it is being explored to selectively inactivate autoantigen-specific T cells with modified autoantigens. However, it has not previously been proposed to use the CD40L receptor on activated T cells to selectively eliminate autoantigen-specific T cells from circulation of autoimmune patients. The present inventors propose a selective method for the treatment of autoimmune diseases such as MS and SLE, that is based on the selective killing of the CD40L-positive autoantigen-specific T cells by an anti-CD40L immunotoxin fusion protein. The significant advantage of the use of an anti-CD40L immunotoxin fusion protein over the use of blocking anti-CD40L Mabs is that after several rounds of anti-CD40L immunotoxin treatment, all autoreactive T cells will have been deleted from the patients T-cell repertoire possibly resulting in a cure from the disease.

The current invention is thus based on the discovery that conjugates of antibodies to human CD40L and a toxin (immunotoxin) can effectively kill cells expressing the CD40L molecule. Accordingly, these anti-CD40L immunotoxins can be used to prevent or treat diseases or conditions that are mediated by the cells expressing the CD40L molecules. Accordingly, it is a primary object of this invention to provide an immunotoxin comprising a Mab capable of binding to the human CD40L antigen located on the surface of activated human lymphocytes and a toxin molecule, wherein the binding of said immunotoxin to the CD40L positive cell results in cell death.

It is another object of this invention to provide a method for treating autoimmune diseases such as multiple sclerosis, psoriasis, rheumatoid arthritis and systemic lupus erythematosus in a patient, the method comprising administering to a patient in need of such treatment a therapeutically effective amount of an immunotoxin capable of binding to the human CD40L antigen located an the surface of activated human lymphocytes, wherein the binding of said immunotoxin to the CD40L antigen results in elimination of the CD40L expressing cells and inhibition of the local inflammatory response, in a pharmaceutically acceptable excipient.

It is a further object of this invention to provide a method for treating malignancies of lymphoid origin in a patient, the method comprising administering to a patient in need of such treatment a therapeutically effective amount of an IT capable of binding to the human CD40L antigen located on the surface of malignant cells of lymphoid origin, wherein the binding of the IT to the CD40L antigen results in elimination of the CD40L expressing tumor cells, in a pharmaceutically acceptable excipient.

DETAILED DESCRIPTION OF THE INVENTION

The invention described herein draws on previously published work and pending patent applications. By way of example, such work consists of scientific papers, patents or pending patent applications. All of these publications and applications, cited previously or below are hereby incorporated by reference.

As used herein, the term "immunotoxin" refers to chimeric molecules in which a cell binding ligand is coupled a toxin or its sub-unit. The toxin portion of the immunotoxin can be derived from various sources, such as plants or bacteria, but toxins of human origin or synthetic toxins (drugs) can be used as well.

Preferably, the toxin part is derived form a plant toxin, such as a ribosome inactivating protein (RIP), type-1 or type-2. A type-2 RIP includes for example ricin (see Olsnes et al, 1982, above). Type-1 RIP's are particularly useful for constructing immunotoxins according to the invention. Type-1 RIP's include pokeweed anti-viral protein (PAP) (reviewed by Irvin, in *Antiviral Proteins in Higher Plants* 65 (1994)), bryodin (see e.g. EP-A-710723, U.S. Pat. No. 5,597,569 and EP-A-725823, GB-A-2194948), momordin (see WO97/19957, WO92/14491, JP-A-51-67714), gelonin (see e.g. WO94/26910, WO93/09130, WO93/20848, WO93/05168), saporin (see Falini et al, 1992, above), and, bouganin (see co-pending patent application PCT/NL98/00336). An example of bacterial toxins is Pseudomonas exotoxin (see EP-A-583794, Allured et al, 1986 above).

The term "ligand" may refer to all molecules capable of binding with or otherwise recognizing a receptor on a target cell. Examples of such ligands include, but are not limited to, antibodies, growth factors, cytokines, hormones and the like, that specifically bind desired target cells.

As used herein, the term "antibody" refers to polyclonal antibodies, monoclonal antibodies, humanized antibodies, single-chain antibodies, and fragments thereof such as Fab, F(ab')2, Fv, and other fragments which retain the antigen binding function of the parent antibody.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv, and others which retain the antigen binding function of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term "humanized antibodies" means that at least a portion of the framework regions of an immunoglobulin are derived from human immunoglobulin sequences.

As used herein, the term "single chain antibodies" refer to antibodies prepared by determining the binding domains (both heavy and light chains) of a binding antibody, and supplying a linking moiety which permits preservation of the binding function. This forms, in essence, a radically abbreviated antibody, having only that part of the variable domain necessary for binding to the antigen. Determination and construction of single chain antibodies are described in U.S. Pat. No. 4,946,778 to Ladner et al., Methods for the generation of antibodies suitable for use in the present invention are well known to those skilled in the art and can be found described in such publications as Harlow & Lane, *Antibodies: A Laboratory Manual*, Cold Spring Harbor Laboratory, (1988).

The immunotoxin molecules of the present invention may be generated by conjugation of a CD40L binding ligand to a toxin by any method known and available to those skilled in the art. The ligand and the toxin molecules may be chemically bonded together by any of a variety of well-known chemical procedures, such as the use of heterobifunctional cross-linkers, e.g. SPDP, carbodiimide or glutaraldehyde. Production of various immunotoxins is well-known within the art and can be found, for example in "*Monoclonal Antibody-Toxin Conjugates*: Aiming the Magic Bullet", Thorpe et al., Monoclonal Antibodies in Clinical Medicine, Academic Press, pp.168–190 (1982) and Waldmann, Science, 252:1657 (1991), both of which are incorporated by reference.

The ligand may also be fused to the toxin by recombinant means such as through the production of single chain antibody-toxin fusion proteins. The genes encoding ligand and the toxin may be cloned in cDNA form and linked directly or separated by a small peptide linker by any cloning procedure known to those skilled in the art. See for example Sambrook et al., *Molecular Cloning: A Laboratory Manual*, Cold Spring Harbor laboratory, (1989).

A person skilled in the art will realize that additional modifications, deletions and insertions may be made to the ligand binding agent and the toxin genes. Especially, deletions or changes may be made in the linker connecting a ligand gene to the toxin. All such constructions may be made by methods of genetic engineering well known to those skilled in the art (see, generally, Sambrook et al., supra) and may produce proteins that have differing properties of affinity, specificity, stability and toxicity that make them particularly suitable for various clinical or biological applications.

The pharmaceutical compositions of this invention are administered at a concentration that is therapeutically effective to a patient in the need of a treatment. To accomplish this goal, the pharmaceutical compositions may be formulated using a variety of acceptable excipients known in the art. The compositions for administration will commonly comprise a solution of the anti-CD40L immunotoxin molecule dissolved in a pharmaceutical acceptable carrier, preferably an aqueous carrier. Typically, the immunotoxins are administered by injection, either intravenously, intraperitoneally, in an other body cavity or or into a lumen of an organ. Methods to accomplish this administration are known to those of ordinary skill in the art. It may also be possible to obtain compositions which may be topically or orally administered, or which may be capable of transmission across mucous membranes.

Before administration to patients, formulants may be added to the antibodies. A liquid formulation is preferred. For example, these formulants may include oils, polymers, vitamins, carbohydrates, amino acids, salts, buffers, albumin, surfactants, or bulking agents. Preferably carbohydrates include sugar or sugar alcohols such as mono-, di-, or polysaccharides. The saccharides can include fructose, glucose, mannose, sorbose, xylose, lactose, maltose, sucrose, dextan, pullulan, dextrin, α- and β-cyclodextrin, soluble starch, hydroxyethyl starch, carboxymethyl cellulose, other water-soluble glucans, or mixtures thereof. Sucrose is most preferred. "Sugar alcohol" is defined as a $C_4$ to $C_8$ hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP Nos. 270,799 and 268,110.

Additionally, antibodies can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546 which are all hereby incorporated by reference in their entireties. Preferred polymers are polyoxyethylated polyols and polyethylene glycol (PEG). PEG is soluble in water at room temperature and has the general formula: R(O—$CH_2$—$CH_2$)$_n$ O—R where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/antibody of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, *J. Biol. Chem.* 263:15064, and a discussion of POG/IL-2 conjugates is found in U.S. Pat. No. 4,766,106, both of which are hereby incorporated by reference in their entireties.

Another drug delivery system for increasing circulatory half-life is the liposome. Methods of preparing liposome delivery systems are discussed in Gabizon et al., *Cancer Research* (1982) 42:4734; Cafiso, *Biochem Biophys Acta* (1981) 649:129; and Szoka, *Ann Rev Biophys Eng* (1980) 9:467. Other drug delivery systems are known in the art and are described in, e.g., Poznansky et al., *Drug delivery systems* (R. L. Juliano, ed., Oxford, N.Y. 1980), pp. 253–315; M. L. Poznansky, *Pharm Revs* (1984) 36:277.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

As stated above, the immunotoxins and compositions of this invention are used to treat human patients. The preferred route of administration is parenterally. In parenteral administration, the compositions of this invention will be formulated in a unit dosage injectable form such as a solution, suspension or emulsion, in association with a pharmaceutically acceptable parenteral vehicle. Such vehicles are inherently nontoxic and nontherapeutic. Examples of such vehicles are saline, Ringer's solution, dextrose solution, and Hanks+ solution. Nonaqueous vehicles such as fixed oils and ethyl oleate may also be used. A preferred vehicle is 5% dextrose in saline. The vehicle may contain minor amounts of additives such as substances that enhance isotonicity and chemical stability, including buffers and preservatives.

The dosage and mode of administration will depend on the individual. Generally, the compositions are administered so that antibodies are given at a dose between 1 :g/kg and 20 mg/kg, more preferably between 20 :g/kg and 10 mg/kg. Preferably, it is given as a bolus dose. Continuous infusion may also be used, if so, the antibodies may be infused at a dose between 1 and 100 :g/kg/min.

The compositions containing the present pharmaceutical compositions or a cocktail thereof (i.e., with other pharmaceutically active proteins) can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose". Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

The present invention will now be illustrated by reference to the following examples which set forth particularly advantageous embodiments. However, it should be noted that these embodiments are illustrative and are not to be construed as restricting the invention in any way.

EXAMPLES

Materials and Methods

Cell Lines and Culture Conditions

The B-cell line JY was cultured in T75 culture flasks routinely (Costar, Cambridge, Mass., USA) in Iscove's modified Dulbecco's medium (IMDM) to which 50 mg/ml gentamycin and 10% foetal calf serum was added (FCS) (Hyclone, Logan, Utah USA). The cells were cultured in a humidified incubator at 37° C. and 5% $CO_2$. Every week the cells were split (1/20 to 1/100). To store the cell line, ampoules were made containing $5-10\times10^6$ cells/ml Hank's balanced salt solution HBSS supplemented with 20% FCS and 10% DMSO and stored in the liquid nitrogen. A subclone of the Jurkatt T-cell line (SPVJ-39.8) constitutively expressing CD40L was cultured under similar condition using glutamine-supplemented RPMI 1640 as culture medium.

Lymphocyte Isolation and Stimulation

Peripheral blood mononuclear cells (PBMC) were isolated from heparinized blood from healthy donors by Ficoll-Hypaque density centrifugation and resuspended in complete medium consisting of RPMI 1640 (Gibco, Paisley, UK) supplemented with 2 mM L-glutamine, streptomycin (100 mg/ml), penicillin (100 U/ml) and 5% heat-inactivated autologous plasma. T cells were further purified from the PBMC preparations by depletion of monocytes, B cells and NK cells using Lumpho-Kwik T (One Lambda, Los Angeles, Calif., USA) according to the manufacturers protocol. For induction of CD40L on T cells, PBMC or purified T-cells were stimulated for 2–6 hours with PMA and ionomycin.

Polymerase Chain Reaction

To amplify DNA fragments, polymerase chain reactions (PCR) were performed. A typical PCR reactions mix contained: 0–10 mM $MgCl_2$, 50 mM KCl, 10 mM Tris-HCl pH 9.0, 1.0% Triton X-100, 0.25 mM dNTP each, 25 pmol primer/100 µl reactions mix, 1–1000 ng DNA/100 µl reaction mix and 2.5 U Taq polymerase. Reactions were run using a Perkin Elmer thermocycler (Perkin Elmer Corp, Norwalk Conn.). A standard PCR scheme consisted of one step for 2–5 min. at 95° C. to denaturate the DNA, followed by 20–40 cycles of 1 min. at 95° C., 1 min. at 55° C. and 1–4 min. at 72° C. After the final step an extension step was performed for 7 min. at 72° C.

Flow Cytometric Analysis

Cells (0.1–0.2×10$^6$/sample) were incubated for 20 min. at 4° C. with the specific Mab (0.1–1 mg/sample). After washing with FACS buffer (PBS pH7.4 1% BSA 0.1% NaN$_3$), the cells were incubated for another 20 min. at 4° C. with goat anti-mouse Mabs conjugated to fluorescein isothiocyanate (FITC) or phycoerythin (PE). The cells were washed with FACS buffer and finally suspended in FACS buffer containing 0.5% paraformaldehyde and analyzed with a FACS can flow cytometer (Becton Dickinson). The specific binding of the monoclonal antibodies is expressed as the mean fluorescent intensity in arbitrary units. A similar protocol was used to test the single chain antibody expressing phage particles. In this case detection was done by using an un-conjugated sheep anti-M13 antibody (Pharmacia Uppsala Sweden), followed after washing by incubation with donkey anti-sheep conjugated to FITC (Sigma Chemical Co. St. Louis, Mo., USA).

Protein Synthesis Inhibition Assays

The cytotoxic effect of the immunotoxins on cells was assessed by measuring their ability to inhibit protein synthesis in a concentration-dependent way. Cells were seeded in a 96-well round bottom plate and incubated with specific Mab alone, Mab and saporin-labeled goat anti-mouse immunoglobulins (GAM-sap), GAM-sap alone, anti-CD40L Mab conjugated to saporin (CD40L-sap) or control Mab conjugated to saporin (Con-sap), for various time intervals. Hereafter [$^3$H]-leucine (1 µCi) was added to each well followed by an overnight incubation. Cells were harvested on glass-wool filters and counted on a beta plate scanner. Cell numbers used were chosen so, that [$^3$H]-leucine incorporation was a linear function of the number of cells. Results were expressed as percentage $^3$H-leucine incorporation with regard to mock-treated cells. The IC$_{50}$ value is the concentration of immunotoxin needed to obtain 50% inhibition of leucine incorporation.

Ribosome inactivation activity of free and conjugated toxins was tested in a reticulocyte lysate system as described by Parente et al. (*Biochem Biophys Acta* 1216:43 (1993)). Reaction mixtures contained, in a final volume of 62.5 µl: 10 mM Tris/HCl buffer, pH 7.4, 100 mM ammonium acetate, 2 mM magnesium acetate, 1 mM ATP, 0.2 mM GTP, 15 mM phosphocreatine, 3 µg of creatine kinase, 0.05 mM amino acids (minus leucine), 89 nCi of L-[$^{14}$C]-leucine, and 25 µl of rabbit reticulocyte lysate. Incubation was at 28° C. for 5 min.

Toxicity to Hematopoietic Progenitor Cells (HPC)

Bone marrow mononuclear cells were resuspended in RPMI 1640 containing 10% AB serum, 2 mM L-glutamine, 100 IU/ml penicillin and 100 µg/ml streptomycin with or without 10$^{-8}$ M, anti-CD40L Mab conjugated to saporin or anti-CD40L Mab and saporin separately. For the enumeration of colony-forming unit-granulocyte/-macrophage (CFU-GM) colonies 100 U/ml GM-CSF and 10 U/ml IL-3 were added, for burst-forming unit-erythroid/macrophage/megakaryocyte (CFU-GEMM) 10 U/ml IL-3 and 3 U/ml Epo. Methylcellulose was added to a final concentration of 0.9%. Finally the cells (200,000) were plated out in 3 cm petri dishes and incubated at 37° C. and 5% CO$_2$. After 14 days colonies of >20 cells were counted.

Example 1

Generation of Chemically Coupled Anti-CD40L Immunotoxins

Anti-CD40L immunotoxins were prepared essentially according to the method described by Tazzari et al. (*Br. J. Haematol.* 81:203 (1992)) and consisted of Mab conjugated to the type-I ribosome-inactivating protein bouganin. The Mab and bouganin were conjugated via a disulfide bond between added sulfhydryl (SH) groups. Briefly, SH groups were introduced separately in the Mabs and in bouganin by 2-iminothiolane treatment. To obtain an optimal bouganin/Mab ratio, the experimental conditions were chosen so, that per bouganin or Mab molecule respectively 1 and 2 SH groups were introduced (respectively 1 and 0.6 mM 2-iminothiolane was added in 50 mM sodium-borate buffer, pH 9). To quantify the amount of bouganin conjugated in the resulting immunotoxin, a trace of $^{125}$I-labelled bouganin was added to the solution. Ellman's reagent was added to determine the number of introduced SH groups and to protect the SH groups to avoid self conjugation of bouganin or Mab. The excess of Ellman's reagent was removed by Sephadex G-25 gel filtration. The modified bouganin was reduced with 20 mM β-mercapto-ethanol to free its SH groups and separated from β-mercapto-ethanol by chromatography on a Sephadex G-25 column and was collected directly onto the unreduced derivatized Mab. After concentration, the conjugation was allowed to proceed for 16 hours at room temperature. The immunotoxins were collected from this reaction mixture by gel filtration on Sephacryl S-200. Conjugation and all gel filtrations were performed in phosphate buffered saline, pH 7.5. The Mab and bouganin content of the immunotoxins was estimated by the absorbance at A$_{280}$ and from the amount of radioactivity.

Example 2

Cloning of Anti-CD40L Monoclonal Antibodies

For the generation of anti-CD40L immunotoxins first the variable heavy (VH) and light chain (VL) of anti-CD40L Mabs are cloned and sequenced. Messenger RNA is prepared from each hybridoma cell line producing anti-CD40L Mabs. Briefly, the cells are lysed after washing in 5 M guanidinium thiocyanate, followed by an incubation with oligo-dT beads in order to bind the mRNA. After elution the mRNA is used in a RT-PCR with degenerated primers either directed against IgG variable light chain or heavy chain to amplify the variable regions. The PCR products are cloned for sequence analysis in a plasmid (PcDNA or pUC18). After DNA sequencing of various clones the consensus heavy and light chain amino acid sequence of anti-CD40L Mabs are obtained.

Example 3

Generation of Recombinant Anti-CD40L Immunotoxins

To obtain a single chain immunotoxin based on anti-CD40L Mab and bouganin, we use a strategy by which a single chain antibody fragment (scFv) is transferred to an expression cassette system containing the pelB leader signal, the cDNA encoding bouganin and a 6× his purification tag. In this expression plasmid, the scFv is cloned between the pelB leader signal and a cDNA encoding the type-I RIP bouganin (Bolognesi et al., *Planta* 203:422 (1997)). In this expression plasmid, the scFv's are cloned between the pelB leader signal and bouganin.

The CD40L-bouganin plasmid contains the Lac promoter that allows the expression of the immunotoxins after IPTG (isopropyl-8-D-thiogalactopyranoside) induction. BL21DE3 bacteria are transformed by the $CaCl_2$ method with the expression plasmid and plated on LB plates containing 100 μg/ml ampicillin. One colony is picked and grow overnight in LB containing 100 μg/ml ampicillin. Next day the culture is diluted (1/100) in LB containing 100 μg/ml ampicillin until the $OD_{600}$ reaches ~0.5. At this point IPTG (Sigma Chemical Co. St. Louis, Mo., USA)(0.1–1 mM) is added. After 3 hours the cells are harvested for purification of the recombinant scFv-immunotoxin. To purify the proteins from the periplasmic space, first the cells are harvested by centrifugation at 4000×g for 20 min. and resuspended in 30 mM Tris/HCl, 20% sucrose, 0.5 mM EDTA, pH 8.0 and incubated on ice for 10 min. Subsequently the cells are centrifugated at 8000×g for 20 min. and resuspended in ice cold 5 mM $MgSO_4$ followed by incubation on ice for 10 min. After centrifugation at 8000×g the supernatant, which contains proteins from the periplasmic space, is collected and dialyzed against 50 mM Na-phosphate, 300 mM NaCl, pH 8.0. This preparation is loaded on a Ni-NTA column (Qiagen, Chatsworth, USA), subsequently the column is washed with 50 mM Na-phosphate, 300 mM NaCl, 10% glycerol, pH 6.0 and elution of the recombinant immunotoxins is done by 50 mM Na-phosphate, 300 mM NaCl, 10% glycerol, pH 4.0. Column fractions are analyzed on SDS-PAGE; fractions containing immunotoxins are pooled and dialyzed against suitable buffer.

The above protocol is intended for use when the immunotoxins are secreted as soluble proteins in the periplasmic space of the bacteria. In case the immunotoxins appear to be insoluble, a similar purification protocol is used based on solubilization of the *E.coli* cells in 6 M guandine hypochloride pH 8.0 followed column steps using 8 M Urea pH 8.0 and pH 6.0 to remove non-specific binding and elation with 8 M Urea pH 4.0. Column fractions containing the recombinant immunotoxins are stepwise dialyzed against a suitable buffer to renatured the proteins.

Example 4

Figure 1:
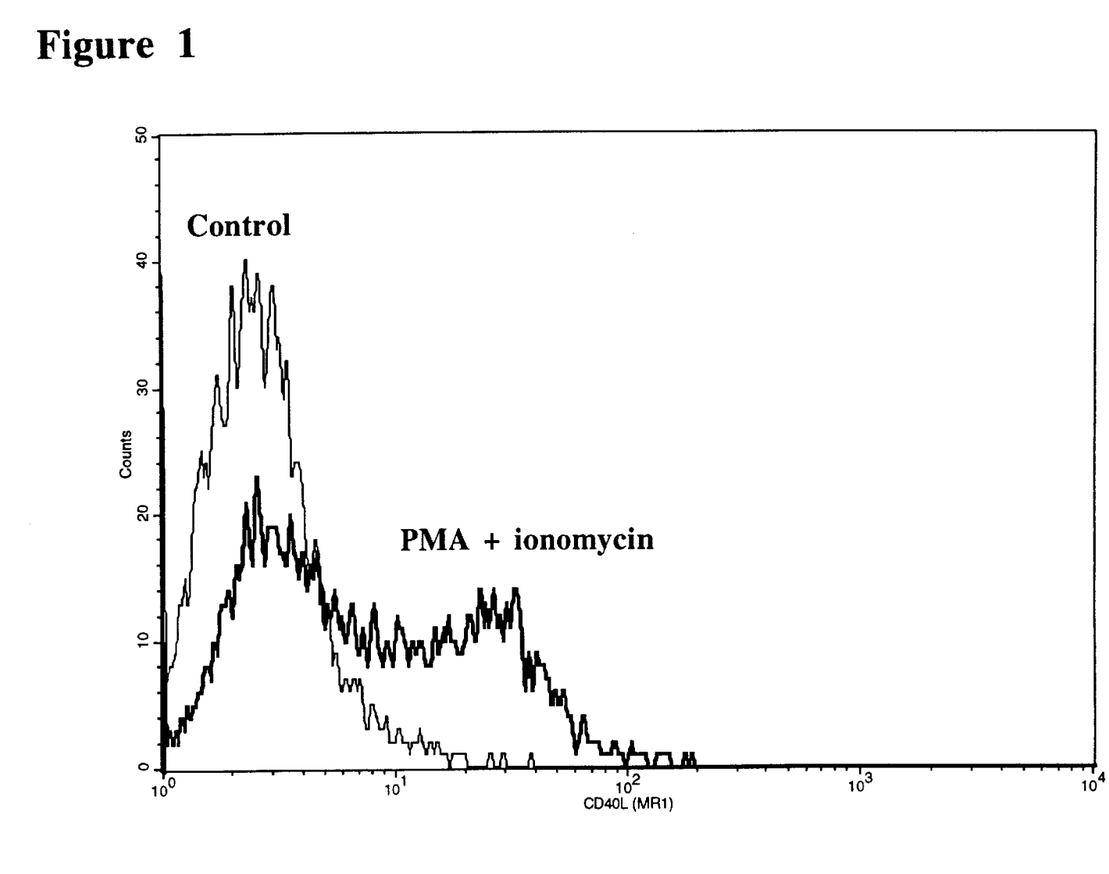
Figure 2:
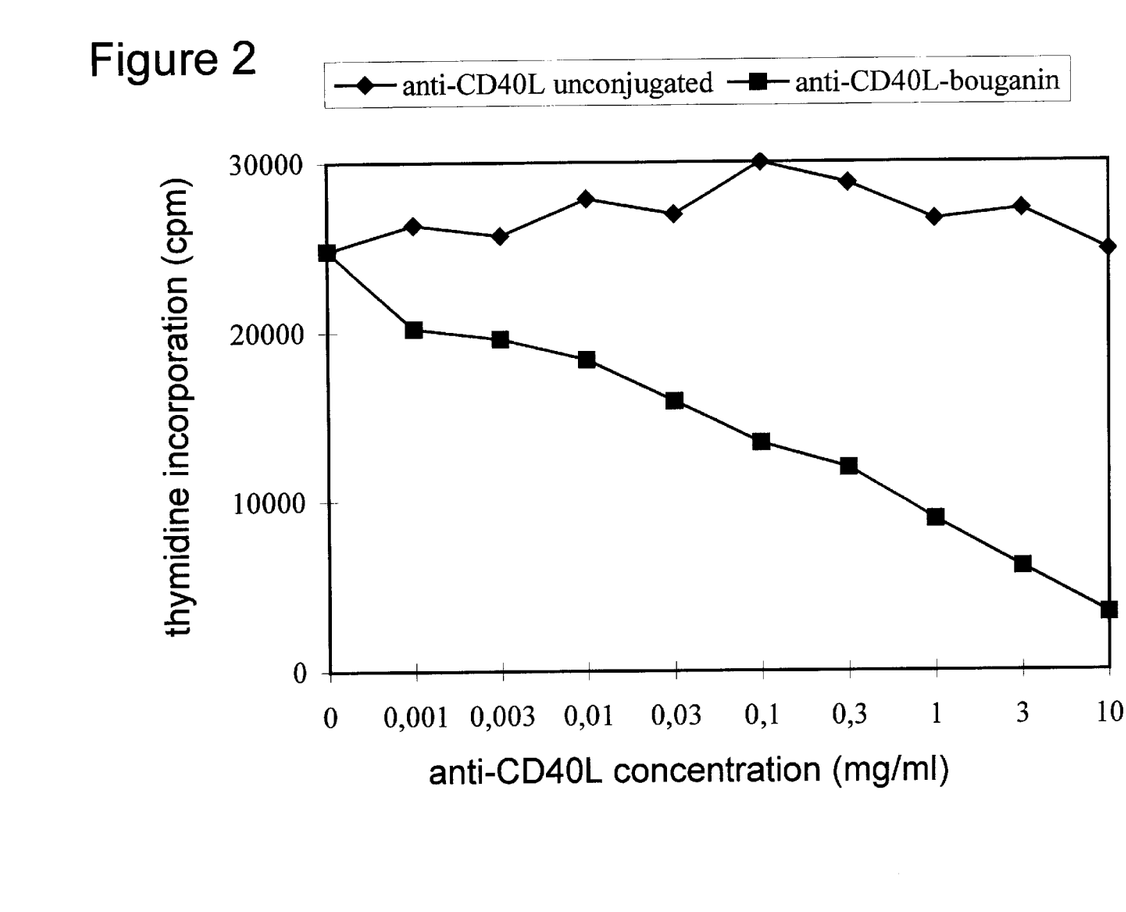

Expression of CD40L on Cell Lines and Toxic Activity of Anti-CD40L Immunotoxins to Cells and Cell Lines To test the activity and specificity of the anti-human CD40L immunotoxins, two cell lines were selected. The first cell line, the Jurkat clone SPVJ-39.8 expresses CD40L on the cell surface. As control we used the CD40L negative JY B-cell line. The cells are cultured as described in the materials and methods section above and analyzed for expression of several cell surface markers. In agreement with the cell surface expression, the anti-human CD40L IT is able to kill the SPVJ-39.8 cells, but not the CD40L-negative JY cells. Additional experiments were performed with an anti-mouse CD40L immunotoxin. The anti-mouse CD40L Mab MR1 was coupled to bouganin as described in the materials and methods section above. The resulting IT was tested for its capacity to inhibit the activation of T cells after stimulation with ionomycin and phorbol-12-myristate 13-acetate (PMA) to induce CD40L on the cells. T cells for this experiment were enriched from splenocytes of Balb/c mice by passing the splenocytes through a nylon wool column. This method yields between 92–95% of $CD3^+$ T cells. Collected cells were resuspended in RPMI with 10% fetal calf serum (FCS) and 100 μM 2-mercaptoethanol. Subsequently, $5 \times 10^6$ cells/ml were then cultured in the presence of mitogenic concentrations of PEA and ionomycin (10 ng/ml and 1 μg/ml respectively) in 96-wells microtiter plates. After 3 hours of incubation at 37° C. in 5% $CO_2$, titrated concentrations of unconjugated anti-CD40L Mab or bouganin-conjugated anti-CD40L Mab were added to the cultures. 3[H]-thymidine was added during the last 8 hours of a 3 day-culture. Incorporation of 3[H]-thymidine into proliferating cells was measured in a beta counter and expressed as counts per min. (cpm) of triplicate cultures. CD40L expression on the isolated T-cells was upregulated after stimulation of PMA and ionomycin, however a subpopulation of the cells remains negative for CD40L after stimulation (FIG. 1). In FIG. 2, it can clearly be seen that the bouganin-conjugated anti-CD40L Mab in contrast to unconjugated anti-CD40L Mab has a potent inhibitory effect on the PMA and ionomycin stimulated T-cells.

Example 5

Figure 3:
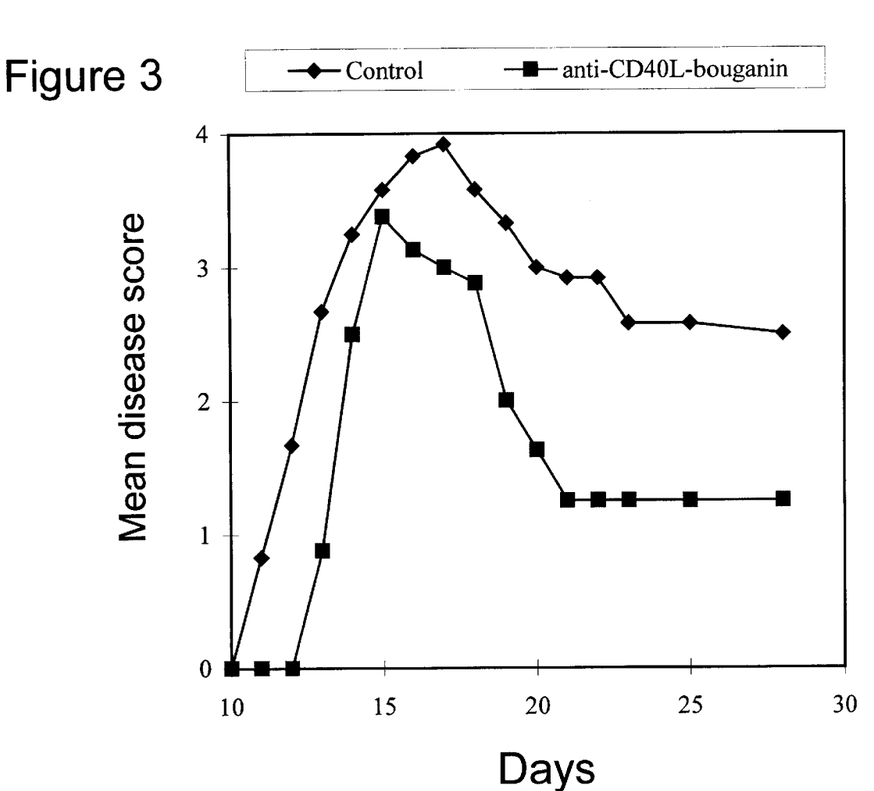

Therapeutic Activity of Anti-CD40L Immunotoxin in a Murine Model for Human Multiple Sclerosis Experimental allergic encephalomyelitis (EAE) is a murine model for human autoimmune disease multiple sclerosis. EAE was induced in inbred female SJL/J mice (9–11 weeks old, Harlan CPB, Zeist, The Netherlands) using PLP 139–151 (HSLGKWLGH PDKF (SEQ. ID. NO.2), Peptides International, Louisville, Ky.). On day 0, the mice were injected in each of their hind foot pads with 50 μl of an emulsion consisting of an equal volume mixture of PLP in phosphate-buffered saline (PBS) and *Mycobacterium tuberculosis* H37-Ra (4 mg/ml, Difco, Detroit, Mich.) in complete Freund's adjuvant (CFA). Pertussis toxin (Sigma, St. Louis, Mo.), 230 ng in 50 μl of PBS, was administered intravenously, at the same time and again 2 days later. Mice were injected intraperitoneally with either unconjugated anti-CD40L Mab at concentrations of 12, 25, 50 or 125 μg in 200 μl of PBS or bouganin-conjugated anti-CD40L Mab at concentrations of 12, 25 or 50 μg on days 0, 2 and 4. EAE signs were scored daily according to the following scale: 0, noclinical disease; 1, flaccid tail; 2, single hind leg paralysis; 3, dual hind leg paralysis; 4, moribund; 5, death. FIG. 3 clearly demonstrates that the bouganin-conjugated anti-mouse CD40L Mab has a potent therapeutic effect at the lowest concentration used 12 μg), since treatment results in a milder and much shorter disease period.

What is claimed is:

1. An immunotoxin molecule comprising an antibody, or a binding fragment thereof, specific for human CD40L antigen conjugated to a Type I ribosome inactivating protein comprising SEQ ID NO 1, wherein the binding of said immunotoxin molecule to the CD40L molecule results in the killing of the CD40L expressing cell.

2. The immunotoxin molecule of claim 1, wherein the antibody is monoclonal, chimeric, human, humanized, bispecific, or a heteroconjugate.

3. The immunotoxin molecule of claim 1, wherein the antibody binding fragment is $F(ab')_2$, $F(ab)_2$, Fab', Fab.

4. A composition comprising the immunotoxin according to claim 1 and a physiologically acceptable diluent, carrier, and/or excipient.

5. The immunotoxin molecule of claim 1, wherein the antibody or binding fragment thereof, and the toxin molecule are encoded by a single recombinant DNA molecule.

6. The immunotoxin molecule of claim 1, wherein the antibody and toxin molecule are expressed in a suitable host cell from a recombinant immunotoxin molecule.

7. An immunotoxin molecule comprising an antibody, or a binding fragment thereof, specific for human CD40L antigen conjugated to a Type I ribosome inactivating protein isolated from *Bougainvillea spectabilis Willd* characterized as having a molecular weight of about 26,000 daltons by polyacrylamide gel electrophoresis under reducing and non-reducing conditions, wherein the binding of said immunotoxin molecule to the CD40L molecule results in the killing of the CD40L expressing cell.

8. The immunotoxin molecule of claim 7, wherein the antibody is monoclonal, chimeric, human, humanized, bispecific, or a heteroconjugate.

9. The immunotoxin molecule of claim 7, wherein the antibody binding fragment is $F(ab')_2$, $F(ab)_2$, Fab', Fab.

10. A composition comprising the immunotoxin according to claim 7 and a physiologically acceptable diluent, carrier, and/or excipient.

11. The immunotoxin molecule of claim 7, wherein the antibody and toxin molecule are expressed in a suitable host cell from a recombinant immunotoxin molecule.

* * * * *